(12) United States Patent
Chiba et al.

(10) Patent No.: US 7,901,465 B2
(45) Date of Patent: Mar. 8, 2011

(54) ONE-PART HAIR DYE COMPOSITION

(75) Inventors: Noboru Chiba, Chuo-ku (JP); Hiroko Okabe, Sumida-ku (JP)

(73) Assignee: Kao Corporation, Tokyo (JP)

(*) Notice: Subject to any disclaimer, the term of this patent is extended or adjusted under 35 U.S.C. 154(b) by 0 days.

(21) Appl. No.: 12/439,333

(22) PCT Filed: Aug. 31, 2007

(86) PCT No.: PCT/JP2007/000940
§ 371 (c)(1),
(2), (4) Date: Feb. 27, 2009

(87) PCT Pub. No.: WO2008/026321
PCT Pub. Date: Mar. 6, 2008

(65) Prior Publication Data
US 2010/0017971 A1    Jan. 28, 2010

(30) Foreign Application Priority Data
Sep. 1, 2006    (JP) ................... 2006-237112

(51) Int. Cl.
*A61Q 5/10*    (2006.01)

(52) U.S. Cl. .............. 8/405; 8/426; 8/455; 8/462; 8/580; 8/617; 8/632

(58) Field of Classification Search ............. 8/405, 426, 8/455, 462, 580, 617, 632
See application file for complete search history.

(56) References Cited

U.S. PATENT DOCUMENTS

| 3,811,830 | A  | * | 5/1974 | DeMarco | 8/405 |
| 2001/0029637 | A1 |   | 10/2001 | Nakashimada et al. | |
| 2002/0144356 | A1 | * | 10/2002 | Kawai et al. | 8/405 |

FOREIGN PATENT DOCUMENTS

| JP | 2-91015 | 3/1990 |
| JP | 5 310543 | 11/1993 |
| JP | 7 165542 | 6/1995 |
| JP | 2001 261533 | 9/2001 |
| JP | 2002 104926 | 4/2002 |
| JP | 2002 205927 | 7/2002 |
| JP | 2006-63015 | 3/2006 |

* cited by examiner

*Primary Examiner* — Eisa B Elhilo
(74) *Attorney, Agent, or Firm* — Oblon, Spivak, McClelland, Maier & Neustadt, L.L.P.

(57) ABSTRACT

An oil-in-water type one-part hair dye composition containing components (A), (B), (C) and (D); (A) a direct dye; (B) a hydrocarbon oil; (C) a polyoxyalkylene-modified dimethylpolysiloxane with an HLB of 7 or higher; and (D) an aromatic alcohol; wherein the content ratio by mass of the component (B) to the component (C), (B)/(C) is 0.05 to 10.

20 Claims, No Drawings

ONE-PART HAIR DYE COMPOSITION

FIELD OF THE INVENTION

The present invention relates to an oil-in-water type one-part hair dye composition.

BACKGROUND OF THE INVENTION

A technology concerning a one-part hair dye composition that colors hair by penetration of a direct dye into the hair, namely a hair manicure, has been heretofore developed. However due to a larger molecular size of the dye, the dye cannot penetrate into the hair easily and the dyeability and the color durability are not satisfactory.

To solve the problem, a solvent promoting the penetration into the hair has been formulated, which has remarkably improved the dyeability and the color durability (Patent Document 1). However, the addition of such solvent has raised another problem that skin is dyed more intensely than hair by the dye due to a structural difference between the hair and the skin.

For solving the problem, a hair dye composition has been proposed, in which as the penetration promoter together with a specific organic solvent a hydrocarbon oil and a polyether-modified silicone are used (Patent Document 2). Thus, coloring of the skin has been slightly reduced, but not yet to a satisfactory level. Further, since the composition according to the Patent Document 2 is a water-in-oil type emulsion, the feel during rinsing is also not fully satisfactory. There is an additional problem that, when formulated into an aerosol type hair dye, the reduction effect on the skin coloring becomes compromised.

Meanwhile, a hair dye composition reducing the skin coloring by using a specific lactone compound has been proposed (Patent Document 3). According to the technology, the skin coloring can be reduced without spoiling the feel during rinsing, but the color durability is not satisfactory and perfumery becomes extremely difficult due to the characteristic odor of the lactone compound.

[Patent Document 1] JP-A-02-91015
[Patent Document 2] JP-A-2002-205927
[Patent Document 3] JP-A-2006-63015

SUMMARY OF THE INVENTION

The present invention provides an oil-in-water type one-part hair dye composition containing components (A), (B), (C) and (D);
(A) a direct dye;
(B) a hydrocarbon oil;
(C) a polyoxyalkylene-modified dimethylpolysiloxane with an HLB of 7 or higher; and
(D) an aromatic alcohol; wherein
the content ratio by mass of the component (B) to the component (C), (B)/(C) is 0.05 to 10.

Further, the present invention provides an aerosol type hair dye composition containing the hair dye composition and (F) a propellant.

DETAILED DESCRIPTION OF THE INVENTION

The present invention relates to a hair dye composition, which hardly dyes the scalp or the skin, is superior in dyeability immediately after dyeing and the color durability as well as the feel of the hair during rinsing and after drying, and has good perfume.

The present inventors have discovered that the problems can be solved by forming an oil-in-water type using together with a direct dye a hydrocarbon oil, a polyoxyalkylene-modified dimethylpolysiloxane with an HLB value equal to or higher than a specific value and an aromatic alcohol at a specific ratio.

Examples of the direct dye of the component (A) include a nitro dye, an anthraquinone dye, an acid dye, an oil-soluble dye and a basic dye.

Examples of the nitro dye include HC Blue No. 2, HC Orange No. 1, HC Red No. 1, HC Red No. 3, HC Yellow No. 2 and HC Yellow No. 4.

Examples of the anthraquinone dye include 1-amino-4-methylaminoanthraquinone and 1,4-diaminoanthraquinone.

Examples of the acid dye include Red No. 2, Red No. 3, Red No. 102, Red No. 104, Red No. 105, Red No. 106, Red No. 201, Red No. 227, Red No. 230, Red No. 232, Red No. 401, Red No. 502, Red No. 503, Red No. 504, Red No. 506, Orange No. 205, Orange No. 206, Orange No. 207, Yellow No. 4, Yellow No. 5, Yellow No. 202, Yellow No. 203, Yellow No. 402, Yellow No. 403, Yellow No. 406, Yellow No. 407, Green No. 3, Green No. 201, Green No. 204, Green No. 205, Green No. 401, Green No. 402, Blue No. 1, Blue No. 2, Blue No. 202, Blue No. 205, Violet No. 401, Black No. 401, Acid Blue 1, Acid Blue 3, Acid Blue 62, Acid Black 52, Acid Brown 13, Acid Green 50, Acid Orange 6, Acid Red 14, Acid Red 35, Acid Red 73, Acid Red 184 and Brilliant Black 1.

Examples of the oil-soluble dye include Red No. 215, Red No. 218, Red No. 225, Orange No. 201, Orange No. 206, Yellow No. 201, Yellow No. 204, Green No. 202, Purple No. 201, Red No. 501, Red No. 505, Orange No. 403, Yellow No. 404, Yellow No. 405 and Blue No. 403. The oil-soluble dye is used for example in a color rinse or a color hair treatment.

Examples of the basic dye include Basic Blue 6, Basic Blue 7, Basic Blue 9, Basic Blue 26, Basic Blue 41, Basic Blue 99, Basic Brown 4, Basic Brown 16, Basic Brown 17, Basic Green 1, Basic Red 2, Basic Red 12, Basic Red 22, Basic Red 51, Basic Red 76, Basic Violet 1, Basic Violet 3, Basic Violet 10, Basic Violet 14, Basic Violet 57, Basic Yellow 57, Basic Yellow 87 and Basic Orange 31.

Among them the acid dye is preferable, and more preferable are Yellow No. 4, Yellow No. 203, Yellow No. 403, Orange No. 205, Green No. 3, Green No. 201, Green No. 204, Red No. 2, Red No. 104, Red No. 106, Red No. 201, Red No. 227, Blue No. 1, Blue No. 205, Purple No. 401, and Black No. 401.

One or more direct dyes may be used and the content thereof in the hair dye composition of the present invention is preferably 0.005 to 5% by mass and more preferably 0.01 to 2% by mass.

The hydrocarbon oil of the component (B) means a hydrocarbon having fluidity at room temperature, and specific examples thereof include squalene, squalane, a liquid isoparaffin, a light liquid isoparaffin, a heavy liquid isoparaffin, an α-olefin oligomer, a liquid paraffin, a cycloparaffin, a vaseline (petrolatum), a paraffin wax, a bee wax, a candellila wax, a cotton wax, a ceresin wax, a carnauba wax, spermaceti, a montan wax, a microcrystalline wax, and a Japan wax. The carbon number of the hydrocarbon oil is preferably 16 to 44, more preferably 18 to 40, even more preferably 20 to 36, and even more preferably 30. The hydrocarbon oils having 30 carbon atoms include squalane, squalene, and a partially hydrogenated squalene. One or more hydrocarbon oils may be used and the content thereof in the hair dye composition of the present invention is preferably 0.05 to 20% by mass, more preferably 0.1 to 10% by mass, and even more preferably 0.1 to 6% by mass from the viewpoints of reduction effect on the coloring of the scalp and skin, as well as a good feel.

The polyoxyalkylene-modified dimethylpolysiloxane with an HLB of 7 or higher of the component (C) has a polyoxyalkylene group, preferably a polyoxyethylene group, bonded to the dimethylpolysiloxane main chain. The HLB is preferably 10 to 18, more preferably 12 to 16, and even more preferably 13 to 15. The HLB is herein defined as follows:

HLB=E/5, where E is the percentage by mass of the polyoxyethylene moiety in a molecule.

Specific examples thereof include silicones KF6011, KF6012, KF6013, KF351A, KF352A and KF615A (Shin-Etsu Chemical Co., Ltd.), silicones SH3746, SH3771C and SH3749 (Dow Corning Toray Co., Ltd.).

One or more polyoxyalkylene-modified dimethylpolysiloxanes of the component (C) may be used and the content thereof in the hair dye composition of the present invention is preferably 0.001 to 30% by mass, more preferably 0.01 to 10% by mass, and even more preferably 0.1 to 21 by mass from the viewpoints of the feel upon application, stability of the system and washability.

The ratio by mass of the component (B) to the component (C) is preferably from 0.05 to 10, more preferably from 0.05 to 7.5, and even more preferably from 0.05 to 5 from the viewpoints of the reduction effect on the skin coloring and the feel during rinsing.

To the hair dye composition of the present invention the aromatic alcohol is added as the component (D) in order to promote penetration of the direct dye into the hair and to enhance the dyeability. Specific examples of the aromatic alcohol include benzyl alcohol, cinnamyl alcohol, phenethyl alcohol, p-anisyl alcohol, p-methylbenzyl alcohol, phenoxyethanol and 2-benzyloxyethanol. Among them, 2-benzyloxyethanol, benzyl alcohol and phenoxyethanol are preferable, and 2-benzyloxyethanol is more preferable.

The content of the aromatic alcohol of the component (D) in the hair dye composition of the present invention is preferably 0.1 to 50% by mass, more preferably 1 to 30% by mass, and even more preferably 5 to 20% by mass.

Furthermore, to improve solubility of the component (D), a lower alcohol or polyol may be added as the component (E). Specific examples thereof include those having 2 to 4 carbon atoms, such as ethanol, 2-propanol, 1-propanol, 1-butanol, ethylene glycol, propylene glycol, isopropylene glycol, 1,3-butylene glycol and glycerin. Two or more lower alcohol or polyol may be used together and the content thereof is preferably 0.1 to 30% by mass and more preferably 0.1 to 15% by mass of the total components.

A high content of the component (D) is preferable to enhance the dyeability immediately after dyeing and the color durability. On the other hand, since the component (D) is poorly soluble in water, the content ratio by mass of the component (D) to the component (E), (D)/(E), is preferably adjusted to 1.25 or less, more preferably 1.1 or less and even more preferably 1 or less from the viewpoint of the storage stability.

Further, it is preferable to add an anionic or nonionic water-soluble polymer to the hair dye composition of the present invention in order to improve the dye usability, such as stability or spreadability upon application. Examples of the anionic polymer include xanthan gum, welan gum, Rhaball gum, Gellan gum, carboxyvinyl polymer, guar gum, an acrylate/methacrylate copolymer and a methyl vinyl ether/maleic anhydride copolymer partially crosslinked by 1,9-decadiene; and examples of the nonionic polymer include polyethylene glycol, hydroxyethyl cellulose, polyvinyl pyrrolidone and a polyvinyl pyrrolidone/vinyl acetate copolymer. Preferable are xanthan gum and Rhaball gum. One or more water-soluble polymers may be used and the content thereof in the hair dye composition of the present invention is preferably 0.01 to 10% by mass, more preferably 0.1 to 5% by mass and even more preferably 0.5 to 3% by mass.

The pH of the hair dye composition of the present invention, when diluted 10-fold by mass with water and in the case, for example, an acid dye is used as the direct dye of the component (A), is preferably 2 to 5, more preferably 2 to 4.5, and even more preferably 2.5 to 4 from the viewpoints of uniform dyeing and mitigated irritation to skin of the hand. As a pH adjuster an organic acid, an inorganic acid and a salt thereof can be used, and an organic acid and a salt thereof are preferable. Examples of the organic acid include citric acid, glycolic acid, succinic acid, tartaric acid, lactic acid, fumaric acid, malic acid, levulinic acid, butyric acid and oxalic acid. Examples of the inorganic acid include phosphoric acid, sulfuric acid and nitric acid. Examples of the salts thereof include a sodium salt, a potassium salt, an ammonium salt and an alkanolamine salt (e.g. a triethanolamine salt). One or more pH adjusters may be used and the content thereof is preferably 0.01 to 10% by mass, more preferably 0.1 to 7% by mass and even more preferably 1 to 5% by mass.

For better hair conditioning activity, an ester oil, a silicone derivative other than the component (C), a higher alcohol and a fatty acid may be added to the hair dye composition of the present invention. Examples of the ester oil include isopropyl palmitate, isopropyl myristate and glyceryl laurate. Examples of the silicone derivative include dimethylpolysiloxane, methylphenylpolysiloxane, an amino-modified silicone and an alkyl-modified silicone. Examples of the higher alcohol include lauryl alcohol, stearyl alcohol, oleyl alcohol and behenyl alcohol. Examples of the fatty acid include lauric acid, stearic acid, oleic acid and behenic acid. One or more of these compounds may be used and the respective contents thereof are preferably 0.1 to 20% by mass, more preferably 0.5 to 10% by mass and even more preferably 1 to 5% by mass. The hair dye composition according to the present invention can be prepared by blending the above-described respective components as well as an aqueous medium as the balance.

The hair dye composition according to the present invention can be used as it is, or used as an aerosol hair dye in combination with a propellant, such as a liquefied gas and a compressed gas. As the propellant, a publicly known liquefied gas or compressed gas used in an ordinary aerosol cosmetic may be used, and a liquefied natural gas (LPG), dimethyl ether (DME), isopentane and a mixture thereof may be exemplified. The content of the propellant in the aerosol hair dye is preferably 1 to 20% by mass, and more preferably 3 to 15% by mass in order to obtain high foamability and an appropriate jet speed. Further, it is preferable to adjust the inner pressure of a filled aerosol can in the range of 0.3 to 0.7 MPa (at 25° C.). In this connection, in the case of an aerosol hair dye, the aforedescribed contents of the components other than the propellant represent the concentrations in the neat liquid (total composition excluding the propellant).

EXAMPLES

Example 1 and Comparative Examples 1 to 3

Each oil-in-water type one-part hair dye composition according to the compositions shown in Table 1 was prepared and evaluation on "hair dyeability", "skin coloring" and "hair smoothness" were carried out.

(Evaluation Methods)

"Hair Dyeability"

The hair dye composition 1 g was evenly applied to a tress of 1 g of white goat hair and left acting at 30° C. for 15 min. Then the tress was rinsed with 40° C. water, subjected to shampooing twice with a shampoo (added with sodium polyoxyethylene alkyl ether sulfate; pH 7), and single treatment with a rinse (added with stearyl trimethylammonium chloride; pH 5), and then dried. The color (immediately after dyeing) was measured by a calorimeter (Colorimeter CR-400 from Minolta) and the results are shown in Table 1.

Thereafter a cycle of 2-times shampooing and 1-time conditioning treatment was repeated 10 cycles, and the tress was dried. The color (after the 10th hair washing) was measured by the calorimeter, and the results are shown in Table 1.

The hair dyeability and the skin coloring described in the next paragraph are expressed herein by the color difference $\Delta E$ in the Lab color system as defined by the following formula. Thereby a higher $\Delta E$ means higher hair dyeability or skin coloring described below. Further, it is broadly known that, if $\Delta E$ values of objects to be measured are different by 2 or higher, the difference of color changes therebetween can be visually clearly recognized.

$$\Delta E = [(\Delta L)^2 + (\Delta a)^2 + (\Delta b)^2]^{1/2}$$

"Skin Coloring"

The hair dye composition was evenly applied to the human brachial region in an amount of 1 g/cm², and left at 30° C. for 15 min. Then the skin was rinsed by warm water, shampooed twice and the color was measured by the calorimeter.

The degree of the skin coloring was rated by the following criteria according to opinions of 10 specialists forming a panel and the results are shown in Table 1. The number of the specialists, who opined that the skin coloring was of no concern, is also shown.

A: 6 or more specialists opined that the skin coloring was no concern.
B: 4 to 5 specialists opined that the skin coloring was no concern.
C: 3 or less specialists opined that the skin coloring was no concern.

"Hair Smoothness After Drying"

To the test tresses made of 5 g of about 15-cm-long untreated Japanese female hair, 2.5 g of the respective hair dye compositions were applied. The tresses were rinsed with warm water, subjected to shampooing and treatment with a rinse, and blow-dried similarly as described above. The hair smoothness was rated during rinsing and after blow-drying by the following criteria according to the opinions of 10 specialists forming a panel and the results are shown in Table 1. The number of the specialists, who opined that the hair was smooth, is also shown.

A: 6 or more specialists opined that the hair was smooth.
B: 4 to 5 specialists opined that the hair was smooth.
C: 3 or less specialists opined that the hair was smooth.

TABLE 1

| | | | Example | Comparative Examples | | |
|---|---|---|---|---|---|---|
| | (% by mass) | | 1 | 1 | 2 | 3 |
| (A) | Black No. 401 | | 0.3 | 0.3 | 0.3 | 0.3 |
| (D) | 2-Benzyloxyethanol | | 7.5 | — | 7.5 | 7.5 |
| | γ-caprolactone | | — | 7.5 | — | — |
| (B) | Squalane | | 5.0 | 5.0 | 0.1 | 5.0 |
| (C) | Polyoxyalkylene-modified dimethylpolysiloxane*[1] | | 1.5 | — | 10.0 | 0.2 |
| | Polyoxyalkylene-modified dimethylpolysiloxane*[2] | | — | 1.5 | — | — |
| (E) | 95% Ethanol | | | 10.0 | | |
| | Xanthan gum | | | 2.0 | | |
| | Lactic acid (90%) | | | 3.0 | | |
| | Sodium hydroxide | | | adjusted to pH 3 (when diluted to 10-fold) | | |
| | Perfume | | | 0.1 | | |
| | Purified water | | | balance | | |
| (B)/(C) | | | 3.3 | — | 0.01 | 25 |
| Evaluation | Hair dyeability (ΔE) | Immediately after dyeing | 53.1 | 52.9 | 53.0 | 51.9 |
| | | After 10th washing | 46.5 | 43.9 | 45.5 | 44.4 |
| | Skin coloring (ΔE) | | 12.1 | 15.7 | 30.1 | 16.1 |
| | | | A | C | C | C |
| | Hair smoothness | During rinsing | 8 | 5 | 4 | 5 |
| | | | A | B | B | B |
| | | After blow-drying | 8 | 7 | 6 | 5 |
| | | | A | A | A | B |

*[1]KF6011 (HLB14.5 Shin-Etsu Chemical Co., Ltd.)
*[2]KF6015 (HLB4.5 Shin-Etsu Chemical Co., Ltd.)

Example 2 and Comparative Examples 4 to 5

The oil-in-water type one-part hair dye compositions according to the compositions shown in Table 2 were prepared and evaluation on "hair dyeability", "skin coloring" and "hair smoothness" were carried out according to the similar methods and criteria as described above.

TABLE 2

|  |  |  | Example | Comparative Examples | |
|---|---|---|---|---|---|
|  | (% by mass) |  | 2 | 4 | 5 |
| (A) | Black No. 401 | | 0.3 | 0.3 | 0.3 |
| (D) | 2-Benzyloxyethanol | | 7.5 | 7.5 | 7.5 |
| (B) | Squalane | | 3.0 | 3.0 | 3.0 |
| (C) | Polyoxyalkylene-modified dimethylpolysiloxane*[1] | | 1.5 | — | — |
|  | Polyoxyalkylene-modified dimethylpolysiloxane*[2] | | — | 1.5 | — |
|  | Polyoxyethylene lauryl ether*[3] | | — | — | 1.5 |
| (E) | 95% Ethanol | | | 10.0 | |
|  | Xanthan gum | | | 2.0 | |
|  | Lactic acid (90%) | | | 3.0 | |
|  | Sodium hydroxide | | | adjusted to pH 3 (when diluted to 10-fold) | |
|  | Perfume | | | 0.1 | |
|  | Purified water | | | balance | |
| (B)/(C) | | | 2.0 | — | — |
| Evaluation | Hair dyeability (ΔE) | Immediately after dyeing | 55.2 | 54.1 | 55.0 |
|  |  | After 10th washing | 47.6 | 46.4 | 45.1 |
|  | Skin coloring (ΔE) |  | 11.3 A | 20.4 C | 32.4 C |
|  | Hair smoothness | During rinsing | 8 A | 3 C | 4 B |
|  |  | After blow-drying | 8 A | 7 A | 4 B |

*[1]KF6011 (HLB14.5 Shin-Etsu Chemical Co., Ltd.)
*[2]KF6015 (HLB4.5 Shin-Etsu Chemical Co., Ltd.)
*[3]Emal 20CM (HLB 13.6 Kao Corp.)

Example 3 and Comparative Example 6

Each oil-in-water type one-part hair dye composition (neat liquid) according to the compositions shown in Table 3 was prepared, and propellant aerosol hair dyes were produced using LPG. The evaluation on "hair dyeability", "skin coloring" and "hair smoothness" were carried out according to the similar methods and criteria as described above.

TABLE 3

|  |  | (% by mass) |  | Example 3 | Comparative Example 6 |
|---|---|---|---|---|---|
| Neat liquid | (A) | Black No. 401 | | 0.3 | 0.3 |
|  | (D) | 2-Benzyloxyethanol | | 7.5 | 7.5 |
|  | (B) | Squalane | | 5.0 | 5.0 |
|  | (C) | Polyoxyalkylene-modified dimethylpolysiloxane*[1] | | 1.5 | — |
|  |  | Polyoxyalkylene-modified dimethylpolysiloxane*[2] | | — | 1.5 |
|  | (E) | 95% Ethanol | | | 10.0 |
|  |  | Xanthan gum | | | 2.0 |
|  |  | Lactic acid (90%) | | | 3.0 |
|  |  | Sodium hydroxide | | | adjusted to pH 3 (when diluted to 10-fold) |
|  |  | Perfume | | | 0.1 |
|  |  | Purified water | | | balance |
|  | Total | | | 100 | 100 |
|  | (B)/(C) | | | 3.3 | — |
| Neat liquid | | | | 93 | 93 |
| Propellant (LPG) | | | | 7 | 7 |
| Total | | | | 100 | 100 |
| Evaluation | Hair dyeability (ΔE) | Immediately after dyeing | | 52.9 | 51.2 |
|  |  | After 10th washing | | 46.3 | 44.0 |
|  | Skin coloring (ΔE) | | | 12.8 A | 18.3 C |
|  | Hair smoothness | when rinsing | | 8 A | 4 B |
|  |  | After blow-drying | | 8 A | 6 A |

*[1]KF6011 (HLB14.5 Shin-Etsu Chemical Co., Ltd.)
*[2]KF6015 (HLB4.5 Shin-Etsu Chemical Co., Ltd.)

With all of the oil-in-water type one-part hair dye compositions described below, the hair dyeability and feel were good and the scalp and skin coloring was negligible.

Example 4

|  | (% by mass) |
|---|---|
| Orange No. 205 | 0.4 |
| Black No. 401 | 0.2 |
| Purple No. 401 | 0.1 |
| Ethanol | 10.0 |
| 2-Benzyloxyethanol | 5.0 |
| Methyl vinyl ether/maleic anhydride copolymer partially crosslinked by 1,9-decadiene | 3.0 |
| Squalane | 3.0 |
| Polyethylene glycol (Mw 2,000,000) | 0.03 |
| Polyethylene glycol (Mw 20,000) | 1.0 |
| Polyoxyalkylene-modified dimethylpolysiloxane*[4] | 2.0 |
| Lactic acid (90%) | 5.0 |

-continued

|  | (% by mass) |
| --- | --- |
| Sodium hydroxide | adjusted to pH 3 (when diluted to 10-fold) |
| Perfume | 0.3 |
| Purified water | balance |
| Total | 100.0 |

*[4] Silicone KF6012 (Shin-Etsu Chemical Co., Ltd.)

Example 5

|  | (% by mass) |
| --- | --- |
| Orange No. 205 | 0.2 |
| Black No. 401 | 0.1 |
| Red No. 227 | 0.2 |
| Ethanol | 5.0 |
| Phenoxyethanol | 1.0 |
| Welan gum | 2.0 |
| Squalane | 1.0 |
| Polyoxyalkylene-modified dimethylpolysiloxane*[5] | 2.0 |
| Citric acid (50%) | 4.0 |
| Sodium hydroxide | adjusted to pH 3 (when diluted to 10-fold) |
| Perfume | 0.3 |
| Purified water | balance |
| Total | 100.0 |

*[5] Silicone SH3746 (Dow Corning Toray Co., Ltd.)

Example 6

|  | (% by mass) |
| --- | --- |
| Orange No. 205 | 0.2 |
| Black No. 401 | 0.1 |
| Red No. 227 | 0.2 |
| Ethanol | 10.0 |
| 2-Benzyloxyethanol | 5.0 |
| Xanthan gum | 2.0 |
| Squalane | 3.0 |
| Polyoxyalkylene-modified dimethylpolysiloxane*[1] | 2.0 |
| Lactic acid | 4.0 |
| Sodium hydroxide | adjusted to pH 3 (when diluted to 10-fold) |
| Perfume | 0.3 |
| Purified water | balance |
| Total | 100.0 |

*[1] Silicone KF6011 (Shin-Etsu Chemical Co., Ltd.)

The invention claimed is:

1. An oil-in-water type one-part hair dye composition, comprising components (A), (B), (C) and (D):
(A) a direct dye;
(B) a hydrocarbon oil selected from the group consisting of squalane, squalene and a partially hydrogenated squalene;
(C) a polyoxyalkylene-modified dimethylpolysiloxane with an HLB of 7 or higher; and
(D) an aromatic alcohol; wherein
the content ratio by mass of the component (B) to the component (C), (B)/(C) is 0.05 to 5.

2. The oil-in-water type one-part hair dye composition according to claim 1, further comprising a lower alcohol or polyol as a component (E).

3. The oil-in-water type one-part hair dye composition according to claim 2, wherein the content ratio by mass of the component (D) to the component (E), (D)/(E) is 1.25 or less.

4. An aerosol type hair dye composition, comprising the oil-in-water type one-part hair dye composition according to claim 1 and (F) a propellant.

5. The oil-in-water type one-part hair dye composition according to claim 1, further comprising a lower alcohol or polyol as a component (E).

6. The oil-in-water type one-part hair dye composition according to claim 5, wherein the content ratio by mass of the component (D) to the component (E), (D)/(E) is 1.25 or less.

7. The oil-in-water type one-part hair dye composition according to claim 1, wherein the direct dye is a nitro dye, an anthraquinone dye, an acid dye, an oil-soluble dye and/or a basic dye.

8. The oil-in-water type one-part hair dye composition according to claim 1, wherein the direct dye is a nitro dye and said nitro dye is selected from the group consisting of HC Blue No. 2, HC Orange No. 1, HC Red No. 1, HC Red No. 3, HC Yellow No. 2 and HC Yellow No. 4.

9. The oil-in-water type one-part hair dye composition according to claim 1, wherein the direct dye is an anthraquinone dye and said anthraquinone dye is selected from the group consisting of 1-amino-4-methylaminoanthraquinone and 1,4-diaminoanthraquinone.

10. The oil-in-water type one-part hair dye composition according to claim 1, wherein the direct dye is an acid dye and said acid dye is selected from the group consisting of Red No. 2, Red No. 3, Red No. 102, Red No. 104, Red No. 105, Red No. 106, Red No. 201, Red No. 227, Red No. 230, Red No. 232, Red No. 401, Red No. 502, Red No. 503, Red No. 504, Red No. 506, Orange No. 205, Orange No. 206, Orange No. 207, Yellow No. 4, Yellow No. 5, Yellow No. 202, Yellow No. 203, Yellow No. 402, Yellow No. 403, Yellow No. 406, Yellow No. 407, Green No. 3, Green No. 201, Green No. 204, Green No. 205, Green No. 401, Green No. 402, Blue No. 1, Blue No. 2, Blue No. 202, Blue No. 205, Violet No. 401, Black No. 401, Acid Blue 1, Acid Blue 3, Acid Blue 62, Acid Black 52, Acid Brown 13, Acid Green 50, Acid Orange 6, Acid Red 14, Acid Red 35, Acid Red 73, Acid Red 184 and Brilliant Black 1.

11. The oil-in-water type one-part hair dye composition according to claim 1, wherein the direct dye is an oil-soluble dye and said oil-soluble dye is selected from the group consisting of Red No. 215, Red No. 218, Red No. 225, Orange No. 201, Orange No. 206, Yellow No. 201, Yellow No. 204, Green No. 202, Purple No. 201, Red No. 501, Red No. 505, Orange No. 403, Yellow No. 404, Yellow No. 405 and Blue No. 403.

12. The oil-in-water type one-part hair dye composition according to claim 1, wherein the direct dye is a basic dye and said basic dye is selected from the group consisting of Basic Blue 6, Basic Blue 7, Basic Blue 9, Basic Blue 26, Basic Blue 41, Basic Blue 99, Basic Brown 4, Basic Brown 16, Basic Brown 17, Basic Green 1, Basic Red 2, Basic Red 12, Basic Red 22, Basic Red 51, Basic Red 76, Basic Violet 1, Basic Violet 3, Basic Violet 10, Basic Violet 14, Basic Violet 57, Basic Yellow 57, Basic Yellow 87 and Basic Orange 31.

13. The oil-in-water type one-part hair dye composition according to claim 1, wherein the direct dye content in the composition ranges from 0.005 to 5% by mass.

14. The oil-in-water type one-part hair dye composition according to claim 1, wherein the hydrocarbon oil content in the composition ranges 0.05 to 20% by mass.

15. The oil-in-water type one-part hair dye composition according to claim 1, wherein the polyoxyalkylene-modified dimethylpolysiloxane with an HLB of 7 or higher has a polyoxyalkylene group bonded to the dimethylpolysiloxane main chain.

16. The oil-in-water type one-part hair dye composition according to claim 15, wherein the polyoxyalkylene group is a polyoxyethylene group.

17. The oil-in-water type one-part hair dye composition according to claim 1, wherein the HLB of the polyoxyalkylene-modified dimethylpolysiloxane ranges from 10 to 18.

18. The oil-in-water type one-part hair dye composition according to claim 1, wherein the content of the polyoxyalkylene-modified dimethylpolysiloxane with an HLB of 7 or higher ranges from 0.001 to 30% by mass.

19. The oil-in-water type one-part hair dye composition according to claim 1, wherein the aromatic alcohol is selected from the group consisting of benzyl alcohol, cinnamyl alcohol, phenethyl alcohol, p-anisyl alcohol, p-methylbenzyl alcohol, phenoxyethanol and 2-benzyloxyethanol.

20. The oil-in-water type one-part hair dye composition according to claim 1, wherein the aromatic alcohol content ranges from 0.1 to 50% by mass.

* * * * *